(12) United States Patent
Burnett et al.

(10) Patent No.: US 10,792,239 B2
(45) Date of Patent: Oct. 6, 2020

(54) WHITE KERATIN COMPOSITIONS

(71) Applicant: KERANETICS LLC, Winston-Salem, NC (US)

(72) Inventors: Luke Burnett, Winston-Salem, NC (US); Elizabeth Kneller, Winston-Salem, NC (US); Erin Falco, Winston-Salem, NC (US)

(73) Assignee: Kernnetics, Inc., Winston-Salem, NC (US)

( * ) Notice: Subject to any disclaimer, the term of this patent is extended or adjusted under 35 U.S.C. 154(b) by 9 days.

(21) Appl. No.: 14/704,211

(22) Filed: May 5, 2015

(65) Prior Publication Data

US 2016/0324750 A1   Nov. 10, 2016
US 2019/0008745 A9   Jan. 10, 2019

Related U.S. Application Data

(63) Continuation of application No. PCT/US2013/068724, filed on Nov. 6, 2013.

(60) Provisional application No. 61/723,030, filed on Nov. 6, 2012.

(51) Int. Cl.
| | |
|---|---|
| *A61K 8/65* | (2006.01) |
| *A61K 35/36* | (2015.01) |
| *A61Q 5/08* | (2006.01) |

(52) U.S. Cl.
CPC ............... *A61K 8/65* (2013.01); *A61K 35/36* (2013.01); *A61Q 5/08* (2013.01)

(58) Field of Classification Search
None
See application file for complete search history.

(56) References Cited

U.S. PATENT DOCUMENTS

| | | | | |
|---|---|---|---|---|
| 2,993,794 | A * | 7/1961 | Moshy | A23J 1/10 |
| | | | | 530/357 |
| 3,464,825 | A * | 9/1969 | Anker | A23J 1/10 |
| | | | | 530/357 |
| 5,358,935 | A | 10/1994 | Smith et al. | |
| 5,651,960 | A * | 7/1997 | Chan | A61K 8/447 |
| | | | | 132/208 |
| 6,251,379 | B1 * | 6/2001 | Omura | A61K 8/046 |
| | | | | 424/401 |
| 2003/0204037 | A1 * | 10/2003 | Van Dyke | A61K 8/891 |
| | | | | 527/200 |
| 2008/0274165 | A1 | 11/2008 | Van Dyke | |
| 2011/0142910 | A1 | 6/2011 | Van Dyke | |
| 2011/0217356 | A1 | 9/2011 | Van Dyke | |
| 2012/0219667 | A1 * | 8/2012 | Kelly | A61K 38/39 |
| | | | | 426/72 |
| 2012/0276188 | A1 * | 11/2012 | Barrows | A61K 35/28 |
| | | | | 424/443 |
| 2015/0011659 | A1 * | 1/2015 | Burnett | A61K 47/42 |
| | | | | 514/773 |
| 2017/0051027 | A1 * | 2/2017 | Van Dyke | A61L 27/227 |

FOREIGN PATENT DOCUMENTS

| | | |
|---|---|---|
| CN | 102 120 753 | 7/2011 |
| GB | 351600 | 7/1931 |
| WO | WO 02/45508 A1 | 6/2002 |
| WO | WO 2007/001339 | 1/2007 |
| WO | WO 2007/050387 | 5/2007 |
| WO | WO 2007/095151 | 8/2007 |
| WO | WO 2007/098053 | 8/2007 |
| WO | WO 2007/098114 | 8/2007 |
| WO | WO 2010/093882 | 8/2010 |
| WO | WO 2011/109808 | 9/2011 |
| WO | WO 2011/112575 | 9/2011 |
| WO | WO 2012/068376 | 5/2012 |
| WO | WO2012/068376 A2 | 5/2012 |
| WO | WO 2013/025928 | 2/2013 |
| WO | WO 2013/025940 | 2/2013 |
| WO | WO 2013/025941 | 2/2013 |
| WO | WO 2016100476 A1 * | 6/2016 ......... A61K 38/1748 |

OTHER PUBLICATIONS

Peters et al., Biochem J, 41: 550-555 (1947).*
De Guzman et al., Biomaterials, 32: 8205-8217 (2011).*
Hill et al., Biomaterials, 31: 585-593 (2010).*
"Sodium sulfite", BASF, http://www.monomers.basf.com/cm/ internet/en/content/Produkte/Technische_Salze/Natriumsulfit accessed on Oct. 4, 2017 (Year: 2017).*
"White", American Heritage Dictionary, https://www.ahdictionary.com/word/search.html? q=whiteet al. accessed Oct. 3, 2017 (Year: 2017).*
Supplementary European Search Report for EP 13853428.4 dated Jun. 24, 2016.
International Search Report for PCT/US2013/068724 dated Feb. 24, 2014.

* cited by examiner

*Primary Examiner* — Abigail Vanhorn

(74) *Attorney, Agent, or Firm* — Massey Law, PLLC

(57) ABSTRACT

The invention provides white keratin protein compositions and methods of making and using white keratin protein compositions.

13 Claims, 8 Drawing Sheets

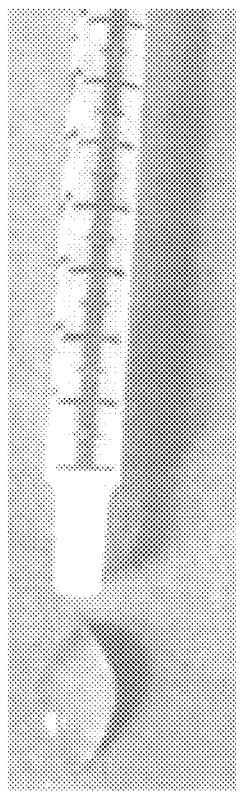 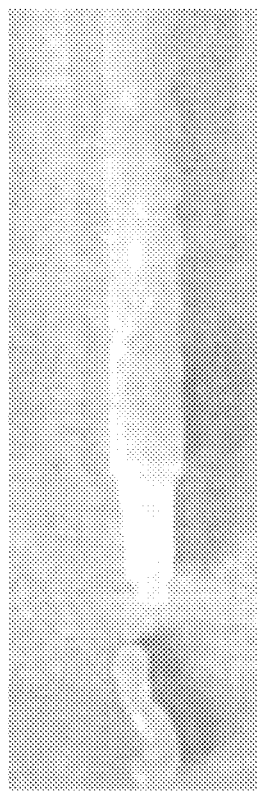 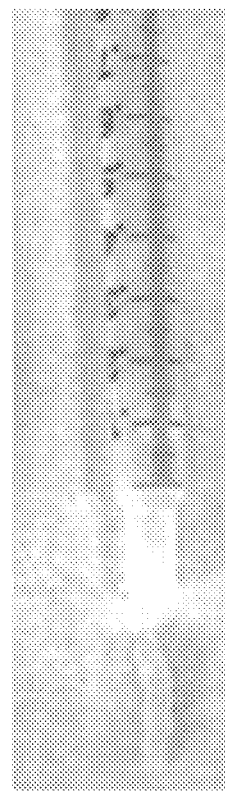
*FIG. 2A*  *FIG. 2B*  *FIG. 2C*

WHITE KERATIN COMPOSITIONS

CROSS REFERENCE TO RELATED APPLICATIONS

This application is a continuation of International Application of PCT/US2013/068724, filed Nov. 6, 2013, which claims priority benefit of U.S. Provisional Patent Application Ser. No. 61/723,030, filed Nov. 6, 2012.

FIELD OF THE INVENTION

This invention relates to compositions of white keratin protein-based biomaterials and methods of making thereof.

BACKGROUND OF THE INVENTION

Keratins are a family of proteins found in the hair, skin, and other tissues of vertebrates. Hair is a unique source of human keratins because it is one of the few human tissues that are readily available and inexpensive. Although other sources of keratins ate acceptable feedstocks for the present invention (e.g. wool, fur, horns, hooves, beaks, others, scales, and the like), human hair is preferred because of its biocompatibility in human medical applications.

Keratins can be extracted from human hair fibers by oxidation or reduction using methods that have been widely published in the art. If one employs a reductive treatment, the resulting keratins are referred to as kerateines. If an oxidative treatment is used, the resulting keratins are referred to as keratoses. These methods typically employ a two-step process whereby the crosslinked structure of keratins is broken down by either oxidation or reduction. In these reactions, the disulfide bonds to cystine amino acid residues are cleaved, rendering the keratins soluble without appreciable disruption of amide bonds. Many of the keratins can remain trapped within the cuticle's protective structure, so a second-step using a denaturing solution is typically employed to elect efficient extraction of the cortical proteins (alternatively, in the case of oxidation reactions, these steps can be combined). This step has also been widely published in the art as solutions such as urea, transition metal hydroxides, surfactant solutions, and combinations thereof have been employed. Common methods employ the use of aqueous solutions of tris(hydroxymethyl) aminomethane in concentrations between 0.1 and 1.0M, and urea solutions between 0.1 and 10M.

When oxidation is selected as the extraction method of choice, strong oxidants are used to cleave the cystine amino acid and solubilize the keratin proteins. A preferred oxidant is peracetic acid. Peracetic acid ($CH_3COOOH$) hydrolyzes into acetic acid ($CH_3COOOH$) and hydrogen peroxide ($H_2O_2$). It also undergoes homolysis to produce peroxyl ($CH_3COOOH$), hydrogen ($H^+$), and hydroxyl ($HO^-$) radicals. Hydroxyl radicals are very strong oxidizing agents due to their high standard reduction potential (2310 mV). When reacted with $HO^-$; proteins decompose into fragments with carbonyl groups (—C=O) in the presence of oxygen ($O_2$) and a small fraction forms protein aggregates via cross-linking. Both of these degraded and cross-linked forms are observed in keratose samples. Aside from oxidation of cystine, peracetic acid (most likely through the action of $HO^-$ and $H_2O_2$)) also reacts and modifies other amino acids of the protein chain. The free thiols (—SH) of cysteines are converted to sulfenic acid (—SOH), which are further oxidized into sulfinic (—$SO_2H$) and sulfonic acid derivatives.

The ability to form a polymerized hydrogel is an important feature in biomaterials used as scaffolds for cells, agents for drug delivery or constructs to promote cell infiltration and tissue remodeling. Hydration of lyophilized keratose materials generally yields the formation of an elastic solid-like hydrogel at high solute concentrations (200 mg/ml in PBS or sterile $H_2O$). Rheological properties of these gels as well as their chemistries indicate that the primary mechanism of gelation is through polymer chain entanglement. Oxidation of free thiols eliminates the ability of oxidized keratins to reassemble via covalent disulfide bonding. Instead, other gelation determinant factors may include electrostatic and hydrophobic interaction. Keratin multimers may form a larger network through electrostatic attraction as suggested in the assembly of intermediate filament molecules in which the head (positive) and the tail (negative) domains of dimers potentially associate to form a tetramer. The negatively-charged sulfonic acid groups can also interact with the basic amino acid residues such as lysine, arginine, and histidine that escaped oxidation. Additionally, the coil regions of keratins that are rich in hydrophobic sequences may aggregate together to increase the polymer molecular weight and promote gelation.

Hair Bleaching

Compounds liberating active oxygen, or oxidizing agents, have long been utilized in bleaching hair. The main examples of such oxidizing agents are hydrogen peroxide or percarbamide, alkali metal perborate, such as sodium perborate, melamine perhydrate, or alkali metal percarbonates, optionally with alkali metal persulfate addition. However, this oxidative treatment of the hair not only bleaches the hair pigment, but also is injurious to the fibrous material of the hair. Evidence of this damage can be found in the numerous and chemical alterations in the hair, of which the most conspicuous are impairment of texture and shine of the hair, increased brittleness, especially breaking of the hair ends, reduction in resistance to splitting and increased alkali solubility of the hair.

Previously described compositions of keratose and kerateine compositions have been reported. However, the dried extracts of keratose and kerateine are generally brown and do not appeal to manufacturers of products meant for use by the ordinary consumer. The brown color is often associated with the notion that the product is dirty or not pure. To combat this assumption, manufacturers often need to add colorants or other additives to change or augment the color of products made with extracted keratose or kerateine. Accordingly, there is a great need to prepare compositions of keratose and kerateine that are white or colorless, but also retain the physiochemical properties that make keratose and kerateine suitable materials for consumer products.

SUMMARY OF THE INVENTION

Disclosed herein are compositions of white or colorless keratin-based biomaterials and methods of making and using such keratin-based biomaterials for various purposes.

BRIEF DESCRIPTION OF THE FIGURES

FIGS. 2A, 2B and 2C depict the gel forming properties of samples of white keratose and standard keratose. Presented in FIG. 2A is a sample of a 5% protein solution of white keratose which forms a hydrogel as exhibited by the bead present when the sample is spotted onto the paper. Presented in FIG. 2B is a sample of a 10% protein solution of white keratose which forms a hydrogel as exhibited by the bead present when the sample is spotted onto the paper. Presented in FIG. 2C is a sample of a 15% protein solution of white keratose which firms a hydrogel as exhibited by the bead present when the sample is spotted onto the paper.

DETAILED DESCRIPTION

Terminology

Figure 1A:
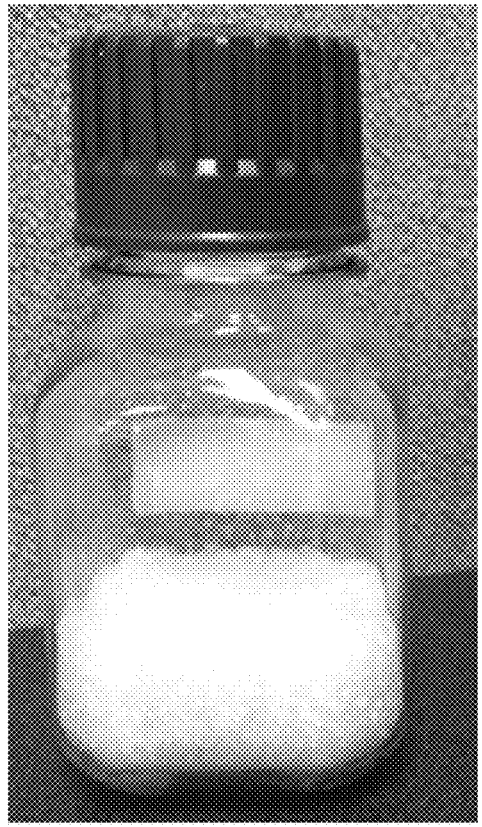
FIGS. 1A and 1B depict the color of white keratose versus standard keratose. Presented in FIG. 1A is a sample of keratose that was purified from bleached human hair (white keratose) (Sample A). Presented in FIG. 1B is a sample of keratin purified from non-bleached human hair (standard keratose) (Sample B). Sample A exhibits a white color while Sample B exhibits a brown color. Other than the bleaching of hair prior to purification of Sample A, both samples were subjected to similar methods of keratose extraction with slight variations.

"Keratin protein source" as used herein includes proteinaceous sources of keratin proteins including but not limited to human or animal wool, fur, horns, hooves, beaks, feathers, scales, and the like.

"Keratin protein(s)" as used herein collectively refers to keratin in keratin protein sources, including but not limited to naturally occurring keratin, reduced keratin, and/or oxidized keratin, or S-sulfonated keratin. This term also refers to the extracted keratin derivatives that are produced by oxidative and/or reductive treatment of keratin, including but not limited to keratose, alpha-keratose, gamma-keratose, kerateine, alpha-kerateine, or gamma-kerateine.

Keratin Protein Sources

Keratins are a family of proteins found in the hair; skin, and other tissues of vertebrates. Hair is a common source of keratins because it is one of the few human materials that are readily available and inexpensive. Other sources of keratins are acceptable feedstocks for the present invention, (e.g., wool, fur, horns, hooves, beaks, feathers, scales, and the like). Human hair is often used with human subjects because of its biocompatibility. Accordingly, in some embodiments, human hair is the keratin protein source. The human hair can be end-cut, as one would typically find in a barber shop or salon.

Hair Bleach Techniques

Compounds liberating active oxygen, or oxidizing agents, have long been utilized in bleaching hair. The main examples of such oxidizing agents are hydrogen peroxide or percarbamide, alkali metal perborate, such as sodium perborate, melamine perhydrate, or alkali metal percarbonates, optionally with alkali metal persulfate addition. Accordingly, in some embodiments, the bleaching compound is hydrogen peroxide.

The degree of bleaching is related to the concentration of bleaching agent used. For example, a hydrogen peroxide solution ranging from about 0.2% to about 10% may be used to bleach the keratin protein source. The degree bleaching is related to the time exposed to the bleaching agent. For example, the keratin protein source may be exposed to a bleaching agent anywhere from 2 min to 10 hours.

Keratin Proteins

Soluble keratins can be extracted from human hair fibers by oxidation or reduction using methods known in the art. These methods typically employ a two-step process whereby the crosslinked structure of keratins is broken down by either oxidation or reduction. In these reactions, the disulfide bonds in cysteine amino acid residues are cleaved, rendering the keratins soluble. The cuticle is essentially unaffected by this treatment, so the majority of the keratins remain trapped within the cuticle's protective structure. In order to extract these keratins, a second step using a denaturing solution is employed. Alternatively, in the case of reduction reactions, these steps can be combined. Denaturing solutions known in the art include urea, transition metal hydroxides, surfactant solutions, and combinations thereof. Common methods used aqueous solutions of tris base (2-Amino-2-(hydroxymethyl)-1,3-propanediol) in concentration between 0.1 and 1.0 M, and urea solutions between 0.1 and 10M, for oxidation and reduction reactions, respectively.

If one employs an oxidative treatment, the resulting keratins are referred to as "keratoses." If a reductive treatment is used, the resulting keratins are referred to as "kerateines."

Crude (unfractionated) extracts of keratins, regardless of redox state, can be further refined into matrix Keratin Associated Proteins ("KAP") and gamma, alpha, and/or charged (acidic or basic) fractions by a variety of methods such as isoelectric precipitation, dialysis, or high performance liquid chromatography (HPLC), as desired. In a crude extract, the alpha fraction begins to precipitate below pH 6 and is essentially completely precipitated by pH 4.2.

In some embodiments, KAP co-precipitate with the alpha fraction, thereby producing an alpha/KAP mixture.

High molecular weight keratins, or "alpha keratins," (alpha helical), are thought to originate from the microfibrillar regions of the hair follicle, and typically range in molecular weight from about 40-85 kiloDaltons (kDa). Low molecular weight keratins, or "gamma keratins," or keratin-associated proteins (globular), are thought to originate from the matrix regions of the hair follicle, and typically range in molecular weight from about 3-30 kiloDaltons for KAP and 10-15 KiloDaltons for gamma keratins.

In some embodiments, the keratin preparations (particularly alpha-keratose or alpha-kerateine) have average monomeric molecular weights of from about 45 to about 70 kDa. Gamma-keratoses and Gamma-kerateines have average molecular weights between 10 and 25 kDa and form complexes with alpha keratins. The alpha keratins extracted and described herein exist as obligate heterodimers that are complexed alpha keratin monomers with higher average molecular weights, e.g., up to 100 or 200 or 300 or 400 or 500 or 600 or 700 or 800 or 900 or 1000 kDa. Theses combinations when complexed (e.g., alpha keratose, gamma keratose, alpha keratein, gamma keratein, or combinations thereof) are termed "metakeratins."

Even though alpha and gamma keratins possess unique properties, the properties of subfamilies of both alpha and gamma keratins can only be revealed through more sophisticated means of purifications and separation such as provided herein. Additional properties that are beneficial emerge and can be optimized upon further separation and purification of crude keratin extracts.

Keratose Production

One method for the production of keratose is by oxidation of keratin with hydrogen peroxide, peracetic acid, or performic acid. In a specific embodiment, the oxidant is peracetic acid. Generally, a solution of peracetic acid is used at a concentration range of about 1% to about 10%. A specific concentration used can be a 2% solution of peracetic acid. In some embodiments, the oxidant concentrations range from a ratio of about 5:1 to about 50:1 weight to weight to the keratin protein source to be extracted. A specific embodiment uses a weight to weight ratio of 30:1 of a 2% peracetic acid solution. Those skilled in the art will recognize that slight modifications to the concentration can be made to affect varying degrees of oxidation, with concomitant alterations in reaction time, temperature, and liquid to solid ratio. Performic acid may offer the advantage of minimal peptide bond cleavage compared to peracetic acid. However, peracetic acid offers the advantages of cost and availability. In some embodiments, the oxidation temperature is between 0 and 100° Celsius. In a specific embodiment, the oxidation temperature is 37° C. In some embodiments, the oxidation time is between 0.5 and 24 hours. In a specific embodiment, the oxidation time is 12 hours. In some embodiments, mechanical mixing is used to maximize oxidation efficiency. Additional yield can be achieved with subsequent extractions with dilute solutions of oxidant, or water. After oxidation, the keratin protein source can be rinsed free of residual oxidant using purified water. In some embodiments, the oxidized keratin protein source is washed with water until residual oxidant is removed. In some embodiments, the washing step is performed until the washed keratin protein source does not test positive for oxidant.

The keratose may be extracted from the oxidized keratin protein source using an aqueous solution of a denaturing agent. Protein denaturants are well known in the art, including but not limited to, urea, transition metal hydroxides (e.g., sodium and potassium hydroxide), ammonium hydroxide, and tris(hydroxymethyl)aminomethane (Tris, also known as Trizma® base). In some embodiments, Tris is used at a ratio of about 5:1 to about 50:1 weight of protein source, to a Tris solution of a concentration of about 0.01 to 1M. In a specific embodiment, the ratio is 25:1. In another specific embodiment, Tris is used at a concentration of 100 mM. Those skilled in the art will recognize that slight modifications to the concentration can be made to effect varying degrees of extraction, with concomitant alterations in reaction time, temperature, and liquid to solid ration. In some embodiments, the extraction temperature is between 0° and 100° C. In a specific embodiment, the extraction temperature is 37° C. In some embodiments, the extraction time is between 0.5 and 24 hours. In a specific embodiment, the extraction time is about 2 hours. Additional yield can be achieved with subsequent extractions with dilute solutions of Tris or purified water. Often, the extraction is performed with mechanical agitation in a mixing tank to ensure a more efficient yield.

Kerateine Production

Similar to the methods described above for extraction and purification of keratoses, kerateines can be produced by reduction of a keratin protein source with thioglycolic acid or beta-mercaptoethanol. Specifically, thioglycolic acid (TGA) is often used. In some embodiments, TGA is added to the keratin protein source at a ratio of about 5:1 to about 50:1. In a specific embodiment, TGA is added at a ratio of 25:1. The TGA is added at a solution ranging in concentrations from about 0.1 to about 10M. In a specific embodiment, the TGA is added in solution at a concentration of 0.5M. During extraction, mechanical agitation is used to maximize extraction efficiency.

The solution containing reductant and extracted kerateine proteins (soluble keratin protein solution) is collected and stored by straining the keratin protein source through a 400 micron mesh and storing the solution at 4° C. A base is then added to the drained keratin protein source in a ratio of about 10:1 to about 50:1. In a specific embodiment, the base is added to the drained keratin protein source at a ratio of 25:1. In some embodiments, the base is Tris generally used at a concentration of about 100 mM. The keratin protein source in the solution with base is mixed with agitation of about 2 hours at 37° C. The solution containing the base and extracted keratin proteins (soluble keratin protein solution) is then filtered through a 400 mm mesh screen then added to the first extracted solution and stored.

Those skilled in the art will recognize that slight modifications to the concentration can be made to effect varying degree of reduction, with concomitant alterations in pH, reaction time, temperature, and liquid to solid ratio. In some embodiments, the reduction is performed at a temperature between 0 and 100° C. In a specific embodiment, the temperature is 37° C. In some embodiments, the reduction time is between 0.5 and 24 hours. In a specific embodiment, the reduction is performed for 8 hours. Unlike the previously described oxidation reaction, reduction is carried out at basic pH. Keratins are highly soluble in a reduction media and are expected to be extracted. The reduction solution may therefore be combined with the subsequent extraction solutions and processed accordingly. Additional yield can be achieved with subsequent extractions with dilute solutions of Tris or purified water. The reduction is carried out with mechanical agitation in a mixing tank to increase the efficiency of the reduction of the keratin proteins.

Residual reductant and denaturing agents can be removed from solution by dialysis. Typical dialysis conditions are 1 to 2% solution of kerateines dialyzed against purified water.

Those skilled in the art will recognize that other methods exist for the removal of low molecular weight contaminants in addition to dialysis (e.g., microfiltration, chromatography, and the like). Once dissolved, the kerateins are stable in solution without the denaturing agent for finite periods. Therefore, the denaturing agent can be removed without the resultant precipitation of kerateines. Regardless of the fractionation/purification process, the resulting kerateines can be concentrated and lyophilized, similar to keratose.

A soluble keratin protein solution is produced by the extraction of keratose and/or kerateine by either oxidative means for keratose, or by reductive means for kerateine.

High Speed Centrifugation

In order to remove many of the keratin associated proteins and other proteins extracted through either oxidative or reductive processes listed above, a high speed centrifugation step is used. Current methods known in the art generally use a low speed centrifugation (around 4,000 rpm) to clear particulate matter. However, this speed does not create enough force to remove many of the beta keratin protein contaminants present in the extracted protein solution. Thus, in some embodiments, high speed centrifugation is employed. Speeds in excess of about 5,000 rpm to about 30,000 rpm can be used. In a specific embodiment, the extracted protein solution is spun at about 20,000 rpm to produce a clarified protein solution of solubilized keratin proteins. In another specific embodiment, the high speed centrifugation step is performed at about 4° C.

A clarified protein solution is produced by the high speed centrifugation and filtration of the soluble keratin protein solution.

Dialysis

In many instances during protein purifications, dialysis is used to separate or even to concentrate certain protein species present in the sample. Accordingly here, in many embodiments, the clarified protein solution is subjected to a dialysis step to fractionate certain protein species. In some embodiments, a 100 kDa molecular weight cutoff membrane is employed in the purification of alpha-keratose or alpha-kerateine. In other embodiments, a 5 kDa molecular weight cutoff membrane is employed to purify gamma-keratose or gamma kerateine. A common matrix for the dialysis membranes is regenerated cellulose, however, many other membrane preparations suitable for protein purification may be used.

In many instances, pressure is applied to aid in the dialysis process. If the pressure applied is too low, the resultant solutions contain greater protein fragments and peptides. Conversely, if the pressure is too high, the result is protein complex degradation. Thus, in some embodiments, the dialysis is performed under conditions that maintain a transmembrane pressure from about 30 to about 70 psi. In some embodiments the transmembrane pressure is about 30 to about 40 psi, in others it is about 60 to about 70 psi. Further, it is important to minimize the heat buildup developed by the shear stress of pressurized dialysis. Thus, in some embodiments, the dialysis is carried out at a temperature from about 4° C. to about 20° C. In a specific embodiment, the dialysis is carried out at about 15° C.

Additionally, as the solution is dialyzed, the conductivity is adjusted. In some embodiments, the conductivity is adjusted down to about or below 0.6 mS. In some instances, the conductivity is adjusted with water.

Lyophilization

Storage of proteins for any length of time can pose stability problems. Since proteins are generally more stable at colder temperatures, maintenance at low temperatures even for short duration is recommended. Typically, proteins can be freeze-dried (lyophilized) to achieve storage conditions while maintaining protein stability.

In some embodiments, lyophilization is used to produce a protein cake of purified protein. The lyophilization is used to stabilize the extracted keratin proteins. Methods known in the art such as shell freezing followed by vacuum or bulk freezing and applying high heat tend to degrade proteins. Accordingly, in some embodiments, a keratin protein cake, comprising keratose alpha or gamma and/or kerateine alpha or gamma is produced by a lyophilization of a clarified keratin protein solution, optionally after dialysis.

In some embodiments, the clarified protein solution post-dialysis is bulk frozen at about −40° C., and then a vacuum is applied until the containment containing the solution reaches about 250 Torr. In some embodiments, heat is then applied in a step-wise fashion, bringing the material to about 0° C., then to about 25° C., then to about 37° C., while maintaining 250 Torr pressure. In some embodiments, the lyophilization process occurs over a 24 hours period.

Grinding

Precise grinding of the lyophilized material aids in the homogeneity of reconstitution and protein stability. Previous methods involve crude grinding methods, including grinding or chopping of the material in a laboratory blender. In the present invention, some embodiments employ a commercial grinding apparatus to machine the material to a homogenous particle size. In some embodiments, a pharmaceutical mill is employed. In other embodiments, the particle size is about 1000 microns or less in diameter.

It is also important to remove the static charge from the ground material to make it easier to work with. Accordingly, in some embodiments, the ground material has been deionized.

Hydrogel Preparation

Hydrogels were prepared for analysis by carefully weighting the appropriate keratin lyophilized powder or powders. The powders were diluted in either sterile phosphobuffer saline or sterile water to generate the described percent mass to volume ratio. These solutions were placed in a 37° C. incubator for 30-90 min before analysis.

In some embodiments, the hydrogel comprises less than 20% protein in a weight to volume ratio. In other embodiments, the hydrogels comprise less than 19%, less than 18%, less than 17%, then 16%, less than 15%, less than 14%, less than 13%, less than 12%, less than 11%, less than 10%, less than 9%, less than 8%, less than 7%, less than 6%, less than 5%, less than 4% protein, or less than 3% in weight to volume ratio.

In other embodiments, the hydrogel comprises about 2%, about 3%, about 4%, about 5%, about 6%, about 7%, about 8%, about 9%, about 10%, about 11%, about 12%, about 13%, about 14%, about 15%, about 16%, about 17%, about 18%, or about 19% protein in a weight to volume ratio. In other embodiments, the hydrogel comprises 2%, 3%, 4%, 5%, 6%, 7%, 8%, 9%, 10%, 11%, 12%, 13%, 14%, 15%, 16%, 17%, 18%, or 19% protein in a weight to volume ratio.

In some embodiments, the hydrogel may comprise 80%, 85%, 90%, 95%, 99% or more keratose. The keratose may be alpha-keratose or gamma-keratose, or some combination thereof. In some embodiments, the keratose in the hydrogel comprises 50%, 55%, 60%, 65%, 70%, 75%, 80%, 85%, 90%, 95%, 99% or more alpha-keratose. In other embodiments, the hydrogel comprises 50%, 55%, 60%, 65%, 70%, 75%, 80%, 85%, 90%, 95%, 99% or more gamma-keratose. In alternative embodiments, the hydrogel is substantially free of gamma-keratose. In some embodiments, the hydrogel is substantially free of kerateine. In other embodiments, keratose-based hydrogels are substantially free of disulfide bonds.

In some embodiments, the hydrogel may comprise 80%, 85%, 90%, 95%, 99% or more kerateine. The kerateine may be alpha-kerateine or gamma-kerateine, or some combination thereof. In some embodiments, the kerateine in the hydrogel comprises 50%, 55%, 60%, 65%, 70%, 75%, 80%, 85%, 90%, 95%, 99% or more alpha-kerateine. In other embodiments, the hydrogel comprises 50%, 55%, 60%, 65%, 70%, 75%, 80%, 85%, 90%, 95%, 99% or more gamma-kerateine. In alternative embodiments, the hydrogel is substantially free of gamma-kerateine. In other embodiments, the hydrogel is substantially free of alpha or gamma-keratose.

In yet embodiments, the hydrogels described herein present similar gelation and stability properties of gels of higher percentage protein concentration than have been previously reported. In some embodiments, compositions of the invention comprise hydrogels of less than 20% protein that exhibit similar gelation and/or stability properties than hydrogels reported in the art that comprise 20% or more protein. In other embodiments, compositions of the invention comprise hydrogels of less than 20% protein that exhibit superior gelation and/or stability properties than hydrogels reported in the art of that comprise 20% or more protein.

In other embodiments, methods of the invention comprise making hydrogels of less than 20% protein. Preparing a hydrogel is described above may comprise the following steps: a) providing keratose, keratein, or a combination thereof, at a concentration of less than 20% weight to volume in an aqueous medium; b) mixing said keratose, kerateine, or a combination thereof in said aqueous medium; and c) allowing the hydrogel to form. Sometimes, the keratose, kerateine, or a combination thereof is provided as a ground protein powder.

In yet other embodiments, methods of the invention comprise making hydrogels of less than 20% protein with slurries of keratose, kerateine or a mixture thereof that have not been subjected to lyophilization. For example, prior to lyophilization, methods of the invention may include forming a hydrogel with a slurry, material retained within the dialysis membrane, material recovered from low-speed centrifugation, or material recovered from a filtration step.

Also, the hydrogels described herein do not require additional biomaterials or added crosslinkers to create or maintain structure. Thus, the compositions presented herein are substantially free of added biomaterials or crosslinkers. Such biomaterials and or crosslinkers include, but are not limited to: albumin, (hydroxyethl)starch, poly-aspartamide, poly(vinyl alcohol), hyaluronic acid, alginate, chitosan, collagen, gelatin, fibrin, silk, poly(ethylene glycol) (aka PEG), poly(lactic acid) (aka PLA), poly(lactic-co-glycolic acid) (aka PLGA), poly(glycolic acid) (aka PGA), poly(dioxanone), poly(caprolacetone), poly(PCPP-SA anhydride), poly(2-hydroxyethl methacrylate) (aka pHEMA), dextran, dextran plus glycidylmethacrylate (GMA), cylco-dextran, dioleyl phosphatidylethanolamine (DOPE) and other catatonic lipids forming nanoparticles, calcium sulphates (bone powders/pastes), glutaraldehyde, 1-ethyl-3-(3-dimethylaminopropyl) carbodiimide) (aka EDC), methylenebisacrylamide, hexamethylenediisocyanate, 1,4-bis(acryloyl)piperazine, 1,4-cyclohexanedimethanol divinyl ether, 1,4-phenylenediaccryloyl chloride, 1,6-hexanediol diacrylate, N-(1-hydroxy-2,2-dimethoxyethyl)acrylamide, di(ethylene glycol) diacrylate, di(ethylene glycol) dimethacrylate, ethylene glycol diacrylate, ethylene glycol dimethacrylate, divinylbenzene, genipin or other common biomaterials or crosslinking agents or agents that are used to bolster structure known in the art. Additional hydrogel forming compositions are described in U.S. Pat. No. 5,854,382.

SPECIFIC EMBODIMENTS

In particular, the composition disclosed herein will comprise keratose, kerateine or a combination thereof, wherein said composition is white. The composition may be substantially free of gamma-keratose or gamma-kerateine. When solubilized in a solvent, the composition may form a colorless solution. The composition may form a hydrogel at a protein concentration of 15% or less, or 10% or less. Said hydrogel may be colorless. The hydrogel may be formed between about 25° C. and about 37° C. and about 37° C. The hydrogel may be stable at about 25° C. to about 37° C. The hydrogel may comprise at least 90% or more keratose. Such a hydrogel may be substantially free of kerateine, and may be substantially free of disulfide bonds. Alternatively, the hydrogel may comprise at least 90% or more kerateine. Such a hydrogel may be substantially free of keratose.

In particular, the composition disclosed herein will comprise keratose, kerateine or a combination thereof, wherein said composition is white. The composition may be substantially free of gamma-keratose or gamma-kerateine. When solubilized in a solvent, the composition may form a colorless solution. The composition may form a hydrogel at a protein concentration of 15% or less, or 10% or less. Said hydrogel may be colorless. The hydrogel may be formed between about 25° C. and about 37° C. and about 37° C. The hydrogel may be stable at about 25° C. to about 37° C. The hydrogel may comprise at least 90% or more keratose. Such a hydrogel may be substantially free of kerateine, and may be substantially free of disulfide bonds. Alternatively, the hydrogel may comprise at least 90% or more kerateine. Such a hydrogel may be substantially free of keratose.

Also disclosed herein is a method of making a composition comprising keratose, kerateine, or a combination thereof, said method comprising;
  a. bleaching a keratin protein source; and
  b. extracting keratose, kerateine or a combination thereof wherein said resultant composition is white.

The composition formed by this method may result in a hydrogel at a protein concentration of less than 15%. The keratin source for the method may be hair, in particular human hair.

The method may further comprise mechanical agitation of the keratin protein source. The method may also comprise a high speed centrifugation step and/or a dialysis step, and/or a lyophilization step. The composition produced by the method may be in powder form.

The composition formed by this method may result in a hydrogel at a protein concentration of less than 15%. The keratin source for the method may be hair, in particular human hair. The method may further comprise mechanical agitation of the keratin protein source. The method may also comprise a high speed centrifugation step, and/or a dialysis step, and/or a lyophilization step. The composition produced by the method may be in powder form.

EXAMPLES

Example I—Preparation of White Keratose

Human hair is washed, dried, and cut into 0.5-1.0 in pieces. 48 oz (3×16 oz buckets) of Clairol Basic White Extra Strength Powder Lightener was added to a 10 gal pail. 96 oz of Salon Care 20-Volume Clear Developer was added to the powder, and the mixture was stirred with a plastic paddle until all the powder lightener was dissolved and a paste was formed. A 500 g bag of hair clippings was manually sprinkled into the lightener and developer paste while mixing to ensure even coverage. Clumps were manually broken up if found. The mixture was then inspected to verify that all hair was coated and that no clumps of hair remained. The mixture was moved to a fume hood for a 40 minute processing time. After 40 minutes, the mixture was removed from the hood, and water was added to the pail to stop the bleaching reaction and to begin the rinse cycle. The clippings, bleaching mixture, and added water were poured from the pail onto a filter screen to allow all hair to be well rinsed using continuous water flow. To ensure complete removal of the bleach solution, pH and conductivity of the rinse water was monitored. Washes continued until the rinse water pH and conductivity reached specifications for purified water.

A cold solution of a 2% PAA solution was added to hair in a mixing tank for 12 hours at 37° C. followed by a wash in 100 mM Tris base. The solution was then centrifuged, filtered, and dialyzed in a custom dialysis system against a 100 kDa molecular weight cutoff cellulose membrane and neutralized to pH 7.4. After dialysis, the solutions were lyophilized, ground into a powder, and processed for terminal sterilization via gamma radiation.

Figure 1B:
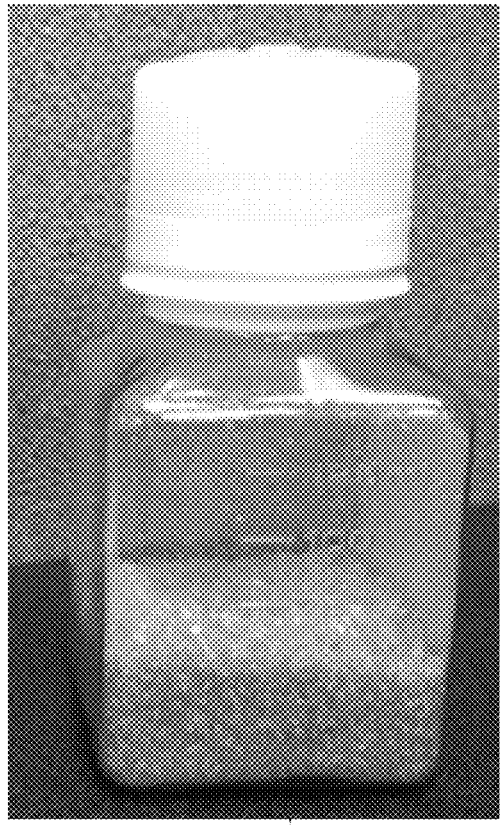

For comparison, keratose was extracted in a similar fashion as outlined above, without the bleaching treatment. The final compositions are represented in FIG. 1. Panel A represents the white keratose composition extracted from the bleached hair. For comparison, Panel B represents a standard keratose composition extracted without the bleaching treatment. The white keratose composition does not have the same brownish color as the standard keratose composition in B that has been extracted by a method excluding a bleach step. Other than the lack of color, the white keratose composition exhibits similar properties to the standard keratose composition in B such as granularity.

Example 2—Preparation of White Kerateine

Similar to the process in Example 1, the extraction of white kerateine involves the initial bleaching step to the hair. Human hair is washed, dried, and cut into 0.5-1 in pieces. 48 oz. (3×16 oz buckets) of Clairol Basic White Extra Strength Powder Lightener was added to a 10 gal pail. 96 oz of Salon Care 20-Volume Clear Developer was added to the powder, and the mixture was stirred with a plastic paddle until all the powder lightener was dissolved and a paste was formed. A 500 g bag of hair clippings was manually sprinkled into the lightener and developer paste while mixing to ensure even coverage. Clumps were manually broken up if found. The mixture was then inspected to verify that all hair was coated and that no clumps of hair remained. The mixture was moved to a fume hood for a 40 minute processing time. After 40 minutes, the mixture was removed from the hood, and water was added to the pail to stop the bleaching reaction and to begin the rinse cycle. The clippings, bleaching mixture, and added water were poured from the pail onto a filter screen to allow all hair to be well rinsed using a continuous water flow. To ensure complete removal of the bleach solution, pH and conductivity of the rinse water was measured. Washes continued until the rinse water pH and conductivity reached specifications for purified water.

A cold solution of a 0.5M thioglycolic acid (TGA) and saturated NaOH was added to hair in mixing tank for 8 hours at 37° C. followed by two washes in 100 mM Tris base and water. A second cycle of TGA/NaOH, base and water washes was carried out. The solution was then centrifuged, filtered, and dialyzed in a custom dialysis system against a 100 kDA molecular weight cutoff polyethersulfone membrane. After dialysis, the solutions were lyophilized, ground into a powder, and sent out for terminal sterilization via gamma radiation.

Example 3: Gel Forming Properties for White Keratose Compositions

In this example, samples of the white keratose compositions from Example 1 were solubilized and examined for gel-forming properties. White keratose solutions were made at various concentrations. 5%, 10%, and 15% solutions of white keratose diluted in PBS or sterile water were made and incubated at 37° C. overnight shaking at 200 rpm in an incubator. Samples from each dilution were then taken and placed in syringes. To test the ability to form a gel, samples were extruded from each syringe onto a piece of paper. If the paper appears wet and/or no bead of gel forms, the sample is characterized as not forming a gel. However, if the paper appears dry surrounding the sample and/or a bead of gel forms, the sample is characterized as forming a gel. Presented in FIG. 2 are the results from this analysis. Presented in A is a sample of a 5% solution of white keratose which forms a hydrogel as exhibited by the bead present when the sample is spotted onto the paper. Presented in B is a sample of a 10% protein solution of white keratose which forms a hydrogel as exhibited by the bead present when the sample is spotted onto the paper. Presented in C is a sample of a 15% protein of white keratose which form a hydrogel as exhibited by the bead present when the sample is spotted onto the paper. These results demonstrate that white keratose compositions at dilutions of 15%, 10% and 5% are capable of forming a gel.

Example 4: Comparison of Rheological Properties of White Keratose and Standard Keratose Compositions Materials and Methods:
White and standard keratose compositions were prepared by the following: keratose alpha and keratose gamma powders were mixed at a 95:5 ratio (e.g., 0.95 g alpha with 0.05 g gamma), and then resuspended in DPBS at a w/v % of 15%. Samples were incubated in a conical tube at 37 degrees C. with or without shaking at 150-200 rpm for a minimum of 16 hours. Following incubation, gels were placed into the cup of Boehlin CS10 rheometer.

Figure 3:
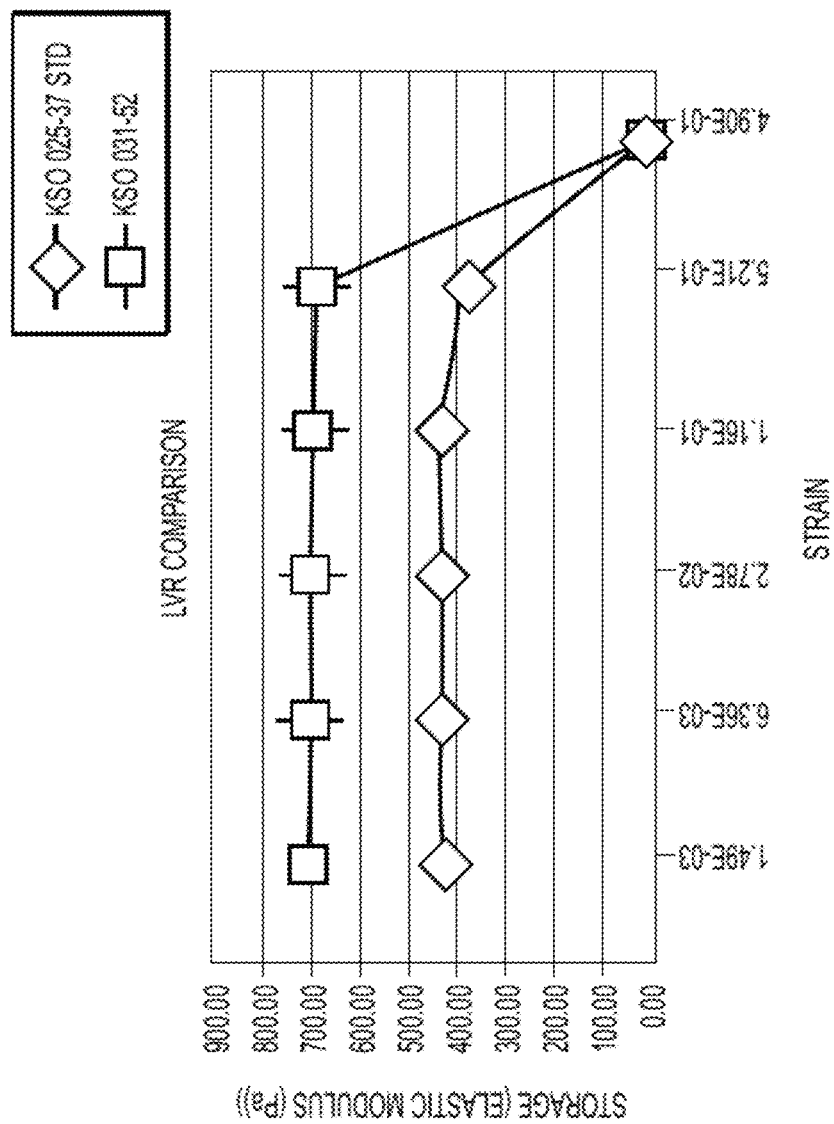
FIG. 3 depicts the linear viscoelastic region comparison of white keratose and standard keratose samples. Presented in the graph are the results of the comparison of standard keratose (KSO 031-52) and white keratose (KSO 025-37 STD). As the stress is increased at a constant frequency of 1 Hz, both samples demonstrated stable storage moduli. Additionally, both samples exhibited a critical drop in moduli at similar strains. However, the white keratose exhibited a lower modulus than the standard keratose sample at all strains tested below the critical drop strain.

Results:
Presented in FIG. 3 are the results from a sweep shear analysis of the two keratose compositions. A sweep of shears (amplitude sweep) was performed with a minimum shear stress of 0.7015 Pa and maximum shear stress of 1000 Pa. The resulting storage modulus was graphed on the y-axis vs. the strain applied. The storage modulus represents stored energy in the material, which is capable of changing in response to mechanical pressure, i.e., elasticity. The graph shows that the elasticity measured for white keratose is higher than the standard keratose sample. This graph also confirms that the samples are comparable in this measurement, because the linear region of elasticity encompasses the same strains between 0.00149 (1.49 E-3) and 0.52119 (5.2 E-2) Pas.

Figure 4:
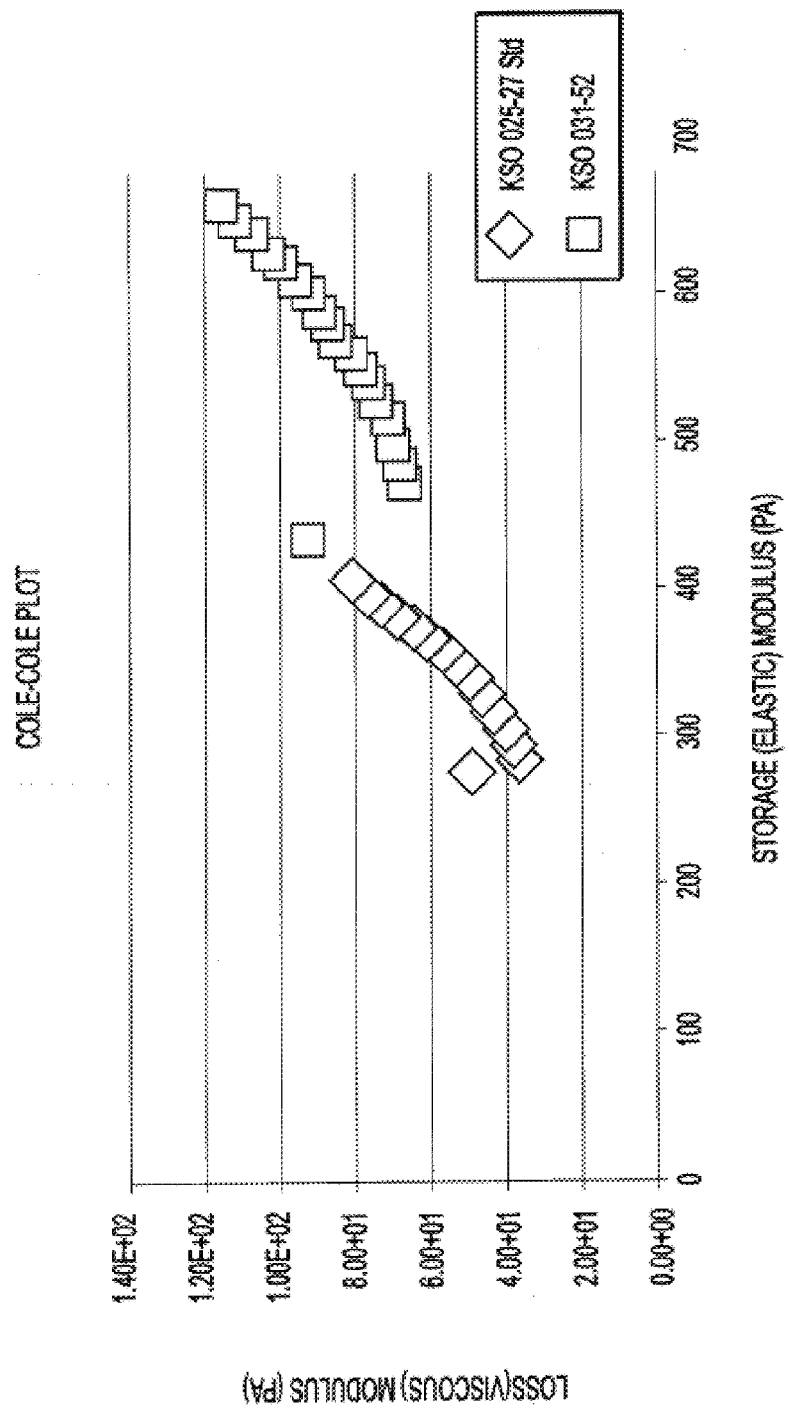
FIG. 4 represents the results from a Cole-Cole comparison of white and standard keratose. Presented in the graph are the results of the comparison of standard keratose (open diamonds) and white keratose (open squares). The white bleached keratose sample exhibited higher viscous and elastic moduli versus the standard keratose. These results suggest that bleached keratose has greater viscoelastic properties than the standard keratose.

Presented in FIG. 4 are the results from a Cole-Cole plot for the two keratose compositions. A Cole-Cole Plot demonstrating the solid (elastic) vs. liquid (viscous) characteristics of the material following a frequency sweep is performed on the material. The white keratose sample shows higher elastic modulus at comparable viscosities, suggesting the white keratose composition has higher elasticity. The overall viscous modulus measurements are also higher for the white keratose sample. Thus, the white keratose sample has both increased viscosity and increased elasticity than the standard keratose sample.

Figure 5:
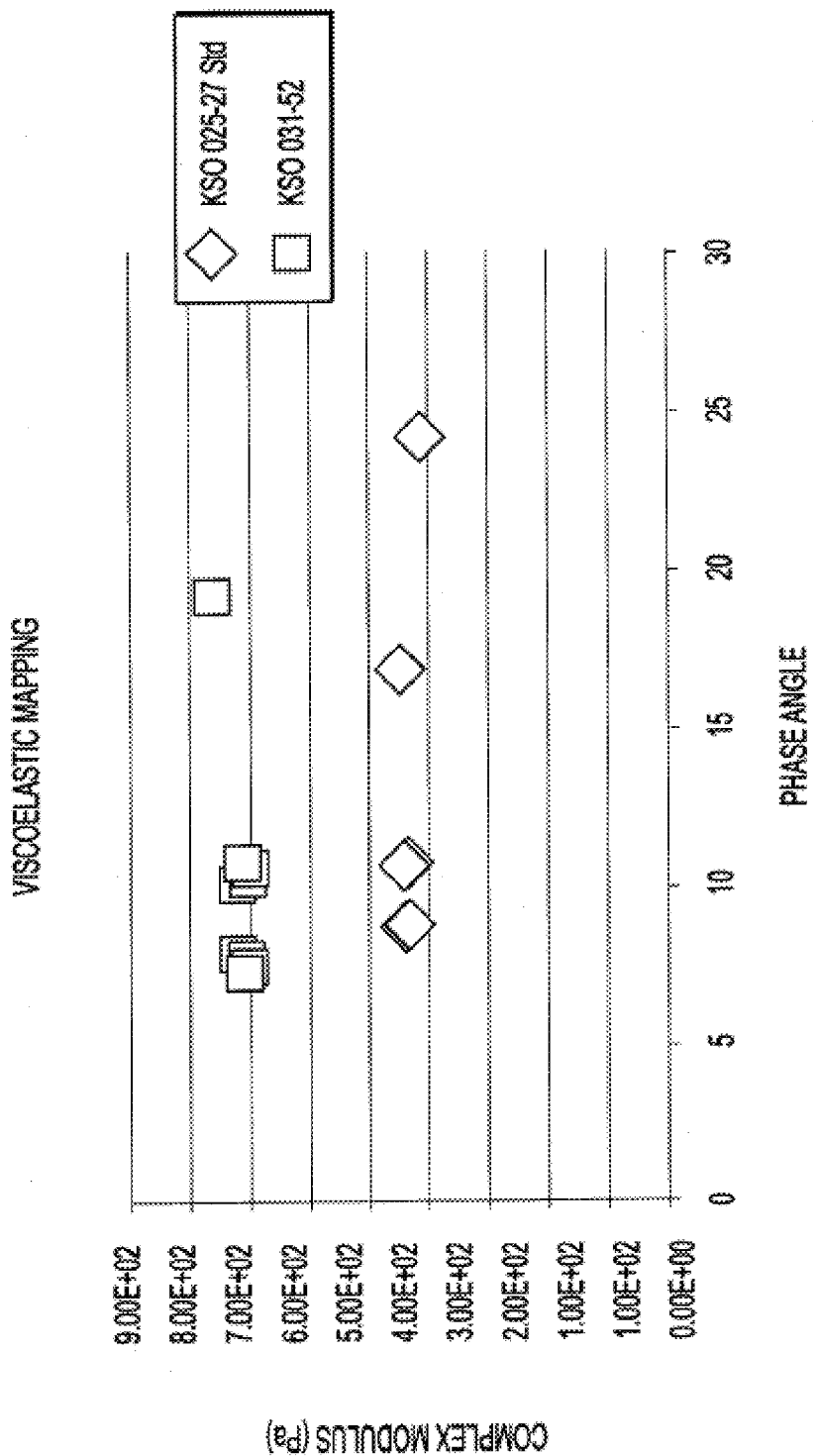
FIG. 5 represents the comparison of the viscoelastic properties of keratose extracted from bleached or non-bleached hair. Presented in the graph are the mapping of viscoelastic properties of standard keratose (open diamonds) and bleached keratose (open squares). Increasing phase angle defines a more elastic sample, while increasing complex modulus means that the sample is becoming more viscous. Both keratose samples exhibited stable viscosities. However, the bleached keratose exhibits greater complex modulus than standard keratose which corresponds to greater viscosity at equivalent percent concentrations.

Presented in FIG. 5 are the results from a frequency sweep analysis of the two keratose compositions. Frequency sweep was performed from 0.1 Hz to 5 Hz to determine viscoelastic mapping phase angle vs. complex modulus. For each phase measurement, the white keratose sample shows both a higher phase angle (defines increasing elasticity) and a higher complex modulus, which signifies both viscous and elastic parameters. Thus, this is another representation of the white keratose sample's increased viscosity and increased elasticity compared with the standard keratose sample.

Figure 6:
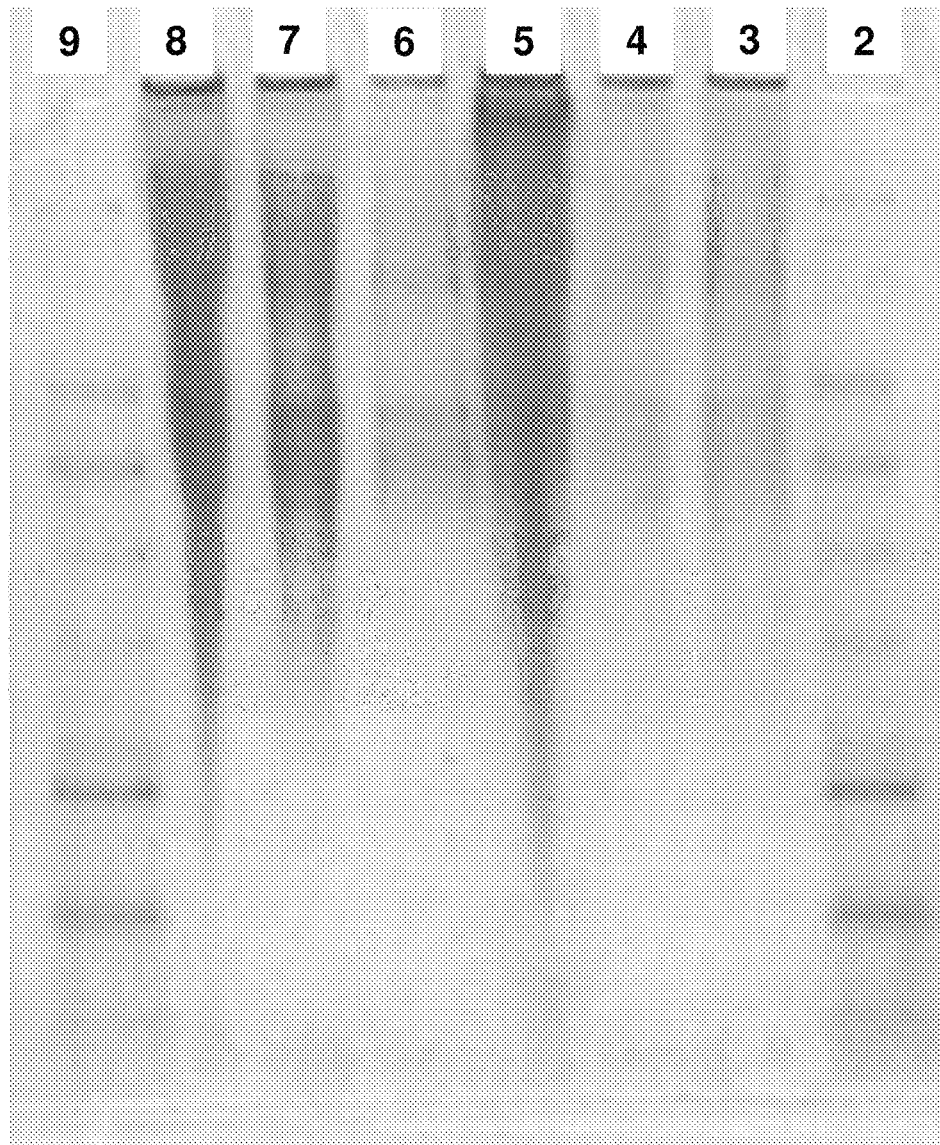
FIG. 6 represents an SDS-PAGE analysis of white and standard keratose. Various concentrations of white keratose (lanes 3, 4, and 5) and standard keratose (lanes 7, 8 and 9) were loaded onto an SDS-Page gel at 25 µg/lane, (lanes 3 and 6), 50 µg/lane (lanes 4 and 7) and 100 µg/lane (lanes 5 and 8). As depicted, the white and standard keratose samples exhibited similar staining patterns when subjected to SDS-Page analysis.

Example 7: SDS Page Comparison of White Keratose and Standard Keratose Compositions The white keratose composition from Example 1 was analyzed by SDS-PAGE chromatography against a standard keratose composition derived from unbleached hair for comparison. The results of the SDS-PAGE analysis are presented in FIG. 6. White keratose (lanes 3, 4 and 5) and standard keratose (lanes 7, 8 and 9) were loaded onto an SDS-Page gel at 25 µg/lane (lanes 3 and 6), 50 µg/lane (lanes 4 and 7) and 100 µg/lane (lanes 5 and 8). A molecular weight ladder was run in lane 2 for comparison. As depicted the white keratose samples and standard keratose samples exhibited similar Coomassie Blue staining patterns. This result suggests that the bleaching process does not alter the protein component makeup in keratose extracted from bleached hair compared keratose extracted from unbleached hair.

Example 8: SEC Analysis of White Keratose and Standard Keratose Compositions

Figure 7A:
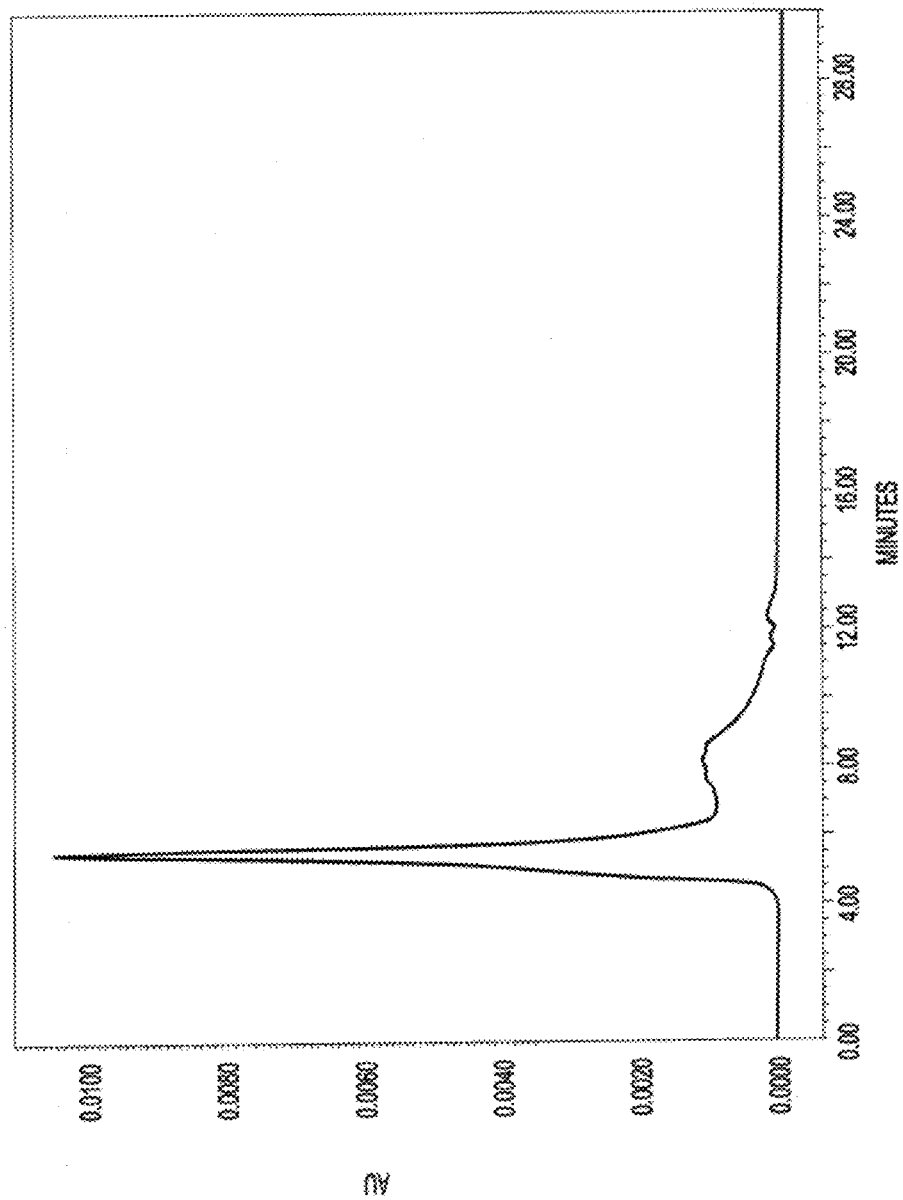
FIGS. 7A and 7B, respectively, represent a Size Exclusion Chromatography (SEC) analysis of white and standard keratose. Presented in FIG. 7A is the tracing of a sample of white keratose. The keratose sample in FIG. 7A demonstrates a single peak on SEC analysis. Presented in FIG. 7B is the tracing of a sample of standard keratose. The keratose sample in FIG. 7B demonstrates a single peak on SEC analysis. Both samples exhibit similar practices when subjected to SEC analysis.
Figure 7B:
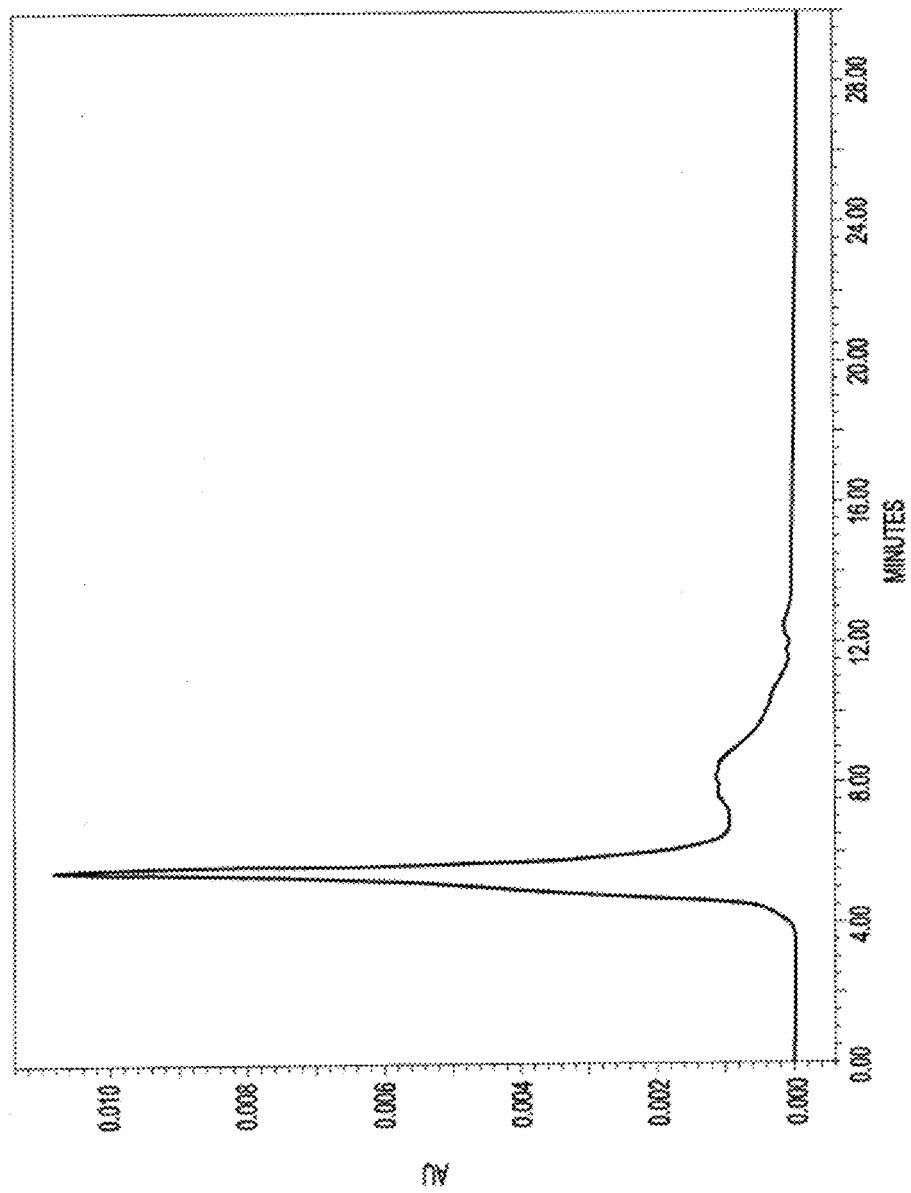

In this Example, samples of white keratose and standard keratose were subjected to Size Exclusion Chromatography analysis. Samples of both compositions were placed over a Waters high-performance liquid chromatography (HPLC) unit equipped with a size exclusion silica column to evaluate the size distribution of proteins that were obtained from the extraction process described in Example 1. Briefly, 10 mg of keratose powder was resuspended in 10 ml of PBS, vortexed, and put in an incubated shaker at 37° C. After 20 min. the solution was mixed with a pipette and placed into the sample vial. The HPLC system was equilibrated with PBS at 0.4 ml/min for 30 minutes prior to testing. 5 µl of the sample solution was injected and rinsed through the column at 0.35 ml/min. The sample absorbance was measured over 30 minutes from 254 nm. FIG. 7 represents the resultant Size Exclusion Chromatography (SEC) analysis of keratose extracted from bleached and non-bleached hair. Presented in A is the tracing of a white keratose sample. The keratose sample in A demonstrates a single peak on SEC analysis. Presented in B is the tracing of a standard keratose sample. The keratose sample in B demonstrates a single peak on SEC analysis. Both samples exhibit similar profiles when subjected to SEC analysis. These results demonstrate that the hair bleaching process does not change or alter the protein component size of white keratose in comparison to standard keratose extracted from unbleached hair.

We claim:

1. A method of making a composition comprising keratose, said method comprising:
   (a) bleaching a keratin protein source with an oxidizing bleaching agent to produce a bleached keratin protein source;
   (b) removing the bleaching agent from the bleached keratin protein source;
   (c) oxidizing the bleached keratin protein source of (b); and
   (d) extracting keratose from the oxidized keratin protein source of (c),
      wherein said composition comprises the keratose extracted at (d),
      wherein a dried form of the composition is white in the absence of added colorants or additives, and
      wherein a solution form of the composition is colorless, said solution form comprising the keratose and a solvent.

2. The method of claim 1, wherein the solution form of the composition forms a hydrogel at a concentration of 2% to 15% weight keratose per volume solvent in the absence of added biomaterials or crosslinkers.

3. The method of claim 1, wherein said keratin protein source is hair.

4. The method of claim 3, wherein said hair is human hair.

5. The method of claim 1, wherein said method comprises mechanical agitation of the bleached keratin protein source.

6. The method of claim 1, wherein said method comprises a high speed centrifugation step.

7. The method of claim 1, wherein said method comprises a dialysis step.

8. The method of claim 1, wherein said method comprises a lyophilization step.

9. The method of claim 1, wherein said composition is in powder form.

10. The method of claim 1, wherein said bleaching agent is hydrogen peroxide.

11. The method of claim 10, wherein the bleached keratin protein source of (b) is oxidized with peracetic acid.

12. The method of claim 1, wherein the bleached keratin protein source of (b) is oxidized with peracetic acid.

13. The method of claim 1, further comprising the step (e) dialyzing the extracted keratose, wherein said composition comprises the extracted and dialyzed keratose.

* * * * *